US011734049B2

(12) United States Patent
Keeth et al.

(10) Patent No.: US 11,734,049 B2
(45) Date of Patent: Aug. 22, 2023

(54) PROTECTED REGIONS MANAGEMENT OF MEMORY

(71) Applicant: Micron Technology, Inc., Boise, ID (US)

(72) Inventors: Brent Keeth, Boise, ID (US); Naveh Malihi, University City, MO (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 17/479,733

(22) Filed: Sep. 20, 2021

(65) Prior Publication Data

US 2022/0004421 A1    Jan. 6, 2022

Related U.S. Application Data

(62) Division of application No. 16/295,708, filed on Mar. 7, 2019, now Pat. No. 11,126,453.

(51) Int. Cl.
*G06F 9/455*          (2018.01)
*H04L 9/14*           (2006.01)
(Continued)

(52) U.S. Cl.
CPC ........ *G06F 9/45558* (2013.01); *G06F 12/145* (2013.01); *H04L 9/14* (2013.01);
(Continued)

(58) Field of Classification Search
CPC .............. G06F 9/45558; G06F 12/145; G06F 21/6245; G06F 2009/45562; G06F 2009/45575; G06F 2009/45583; G06F 2009/45587; G06F 2212/1052; G06F 12/1466; G06F 21/6218; G06F 12/1458; G06F 21/604; H04L 9/14; H04L 9/088
See application file for complete search history.

(56) References Cited

U.S. PATENT DOCUMENTS 7,278,030 B1    10/2007   Chen et al.
9,229,651 B2    1/2016    Min et al.
(Continued)

FOREIGN PATENT DOCUMENTS

KR    1020140078390    6/2014

OTHER PUBLICATIONS

International Search Report and Written Opinion for related PCT Application No. PCT/US2020/017578, dated Jun. 5, 2020, 13 pages.

*Primary Examiner* — Sisley N Kim
(74) *Attorney, Agent, or Firm* — Brooks, Cameron & Huebsch, PLLC (57) ABSTRACT

Apparatuses and methods related to managing regions of memory are described. Managing regions can include verifying whether an access command is authorized to access a particular region of a memory array, which may have some regions that have rules or restrictions governing access (e.g., so-called "protected regions"). The authorization can be verified utilizing a key and a memory address corresponding to the access command. If an access command is authorized to access a region, then a row of the memory array corresponding to the access command can be activated. If an access command is not authorized to access the region, then a row of the memory array corresponding to the access command may not be activated.

17 Claims, 5 Drawing Sheets

(51) Int. Cl.
 *G06F 12/14* (2006.01)
 *G06F 21/62* (2013.01)

(52) U.S. Cl.
 CPC ............ *G06F 21/6245* (2013.01); *G06F 2009/45562* (2013.01); *G06F 2009/45575* (2013.01); *G06F 2009/45583* (2013.01); *G06F 2009/45587* (2013.01); *G06F 2212/1052* (2013.01)

(56) References Cited

U.S. PATENT DOCUMENTS

| | | |
|---|---|---|
| 11,182,473 B1* | 11/2021 | Ha .................. G06F 9/45558 |
| 2002/0124148 A1 | 9/2002 | Beukema et al. |
| 2003/0093624 A1 | 5/2003 | Beukema et al. |
| 2006/0294288 A1* | 12/2006 | Seth .................. G06F 12/1441 711/6 |
| 2007/0067590 A1 | 3/2007 | Savagaonkar et al. |
| 2009/0037682 A1 | 2/2009 | Armstrong et al. |
| 2009/0164991 A1 | 6/2009 | Takashige et al. |
| 2012/0233378 A1 | 9/2012 | Elteto |
| 2014/0380009 A1 | 12/2014 | Lemay et al. |
| 2015/0319160 A1 | 11/2015 | Ferguson et al. |
| 2016/0239430 A1 | 8/2016 | Tsirkin et al. |
| 2017/0132156 A1 | 5/2017 | Axnix et al. |
| 2017/0277898 A1 | 9/2017 | Powell et al. |

\* cited by examiner

PROTECTED REGIONS MANAGEMENT OF MEMORY

PRIORITY INFORMATION

This application is a Divisional of U.S. application Ser. No. 16/295,708, filed Mar. 7, 2019, which issues as U.S. Pat. No. 11,126,453 on Sep. 21, 2021, the contents of which are included herein by reference.

TECHNICAL FIELD

The present disclosure relates generally to memory, and more particularly to apparatuses and methods associated with managing protected regions of memory.

BACKGROUND

Memory devices are typically provided as internal, semiconductor, integrated circuits in computers or other electronic devices. There are many different types of memory including volatile and non-volatile memory. Volatile memory can require power to maintain its data and includes random-access memory (RAM), dynamic random-access memory (DRAM), and synchronous dynamic random-access memory (SDRAM), among others. Non-volatile memory can provide persistent data by retaining stored data when not powered and can include NAND flash memory, NOR flash memory, read only memory (ROM), Electrically Erasable Programmable ROM (EEPROM), Erasable Programmable ROM (EPROM), and resistance variable memory such as phase change random-access memory (PCRAM), resistive random-access memory (RRAM), and magnetoresistive random-access memory (MRAM), among others.

Memory is also utilized as volatile and non-volatile data storage for a wide range of electronic applications including, but not limited to, personal computers, portable memory sticks, digital cameras, cellular telephones, portable music players such as MP3 players, movie players, and other electronic devices. Memory cells can be arranged into arrays, with the arrays being used in memory devices.

Various computing systems include a number of processing resources that are coupled to memory (e.g., a memory system), which is accessed in association with executing a set of instructions (e.g., a program, applications, etc.). For various reasons, it can be desirable to prevent unauthorized access to memory (e.g., via read and/or write operations) or particular portions thereof. For instance, a memory system may store sensitive data (e.g., data desired to be kept secret, such as passwords, personal information, etc.).

DETAILED DESCRIPTION

The present disclosure includes apparatuses and methods related to managing protected regions of memory. Access commands can be provided from a host to a memory device. The memory device may rely on the host for implementing security measures to prevent unauthorized access to the memory device. However, implementing security measures at the memory device may further improve security and may mitigate unauthorized memory accesses.

In various embodiments, a memory device can mitigate unauthorized memory accesses by verifying access commands as authorized utilizing credentials provided along with, or as part of, the access commands. The credentials can be stored in a plurality of registers implemented in the memory device prior to receipt of the access command (e.g., from a host). As used herein, an access command can include one or more sub-commands. For example, an access command can include a pre-charge command, an activate command, a read command, and/or a write command, among other possible commands.

The authorization of an access command can be verified utilizing a key (e.g., credential(s)). The access command can request access to an address and/or a plurality of addresses. The memory device can determine whether the address is locked or unlocked based on a security mode associated with the address. If the address is locked, then the memory device can refrain from providing access to the address unless a key associated with the access command is also provided to the memory device. The key can be verified against a stored key to determine whether to unlock the address.

If the key matches the stored key, then the memory device can unlock the address and can provide access to the address(es). If the key does not match the stored key, then the memory device can refrain from providing access to the address(es).

In various embodiments, a memory system can include one or more protected regions. The memory system can comprise different sets of registers for each of the protected regions. Each of the protected regions of the memory system can be managed by a hypervisor. The hypervisor can assign the protected regions to a plurality of virtual machines (VM) such that the VMs can share a memory resource comprising the protected regions. The protected regions of the shared memory resource can be allocated among the VMs such that the VMs are segregated from each other. That is, a protected region allocated to one VM is inaccessible by the other VMs. For example, in a number of embodiments, a key exchange procedure can be implemented to prevent VMs from accessing address space allocated to another (e.g., different) VM. For instance, an access command/request, by a particular VM, to an address space within a protected region of the shared memory resource, can be granted or denied based on a key comparison. In this manner, even though multiple VMs may have access to a common memory space, particular regions of the common space can be segregated from other regions to prevent unauthorized access by one VM from an address space designated only for another VM.

Implementing security measures at a memory device to prevent unauthorized access can increase the security of the memory device beyond the security which may be provided by a host. For example, unauthorized access commands may be prevented from accessing the memory device by security measures implemented at a host as well as by security measures implemented at a memory device.

In various examples, data can be protected responsive to detection of an unauthorized access attempt. An unauthorized access attempt can comprise an access command to a protected region without providing a key corresponding to the protected region. For example, a VM can provide an access command to a protected region that is not assigned to the VM. Said access command may be considered unauthorized, for example, because the VM provides a key which does not match a key corresponding to the protected region, or because the VM fails to provide a key in association with the access command.

A security mode corresponding to a protected region of a memory array storing the data can be modified responsive to the detection of the unauthorized access attempts. The protected region can be placed in a first security mode from a second security mode where the first security mode is a more heightened security mode than the second security mode. The data can be moved to a different protection region and/or an unprotected region responsive to the detection of the unauthorized access attempts. In some examples, a power status of a computing device comprising the memory array can be modified responsive to the detection of the unauthorized access attempts. The computing device can be shut down or placed in a sleep state. Responsive to detecting the unauthorized access attempts, the memory device targeted by the access attempt or the computing device comprising the memory device can be locked to prevent access to the memory device and/or the computing device.

As used herein, "a number of" something can refer to one or more of such things. For example, a number of memory devices can refer to one or more memory devices. A "plurality" of something intends two or more. Additionally, designators such as "N," as used herein, particularly with respect to reference numerals in the drawings, indicates that a number of the particular feature so designated can be included with a number of embodiments of the present disclosure.

The figures herein follow a numbering convention in which the first digit or digits correspond to the drawing figure number and the remaining digits identify an element or component in the drawing. Similar elements or components between different figures may be identified by the use of similar digits. As will be appreciated, elements shown in the various embodiments herein can be added, exchanged, and/or eliminated so as to provide a number of additional embodiments of the present disclosure. In addition, the proportion and the relative scale of the elements provided in the figures are intended to illustrate various embodiments of the present disclosure and are not to be used in a limiting sense.

Figure 1A:
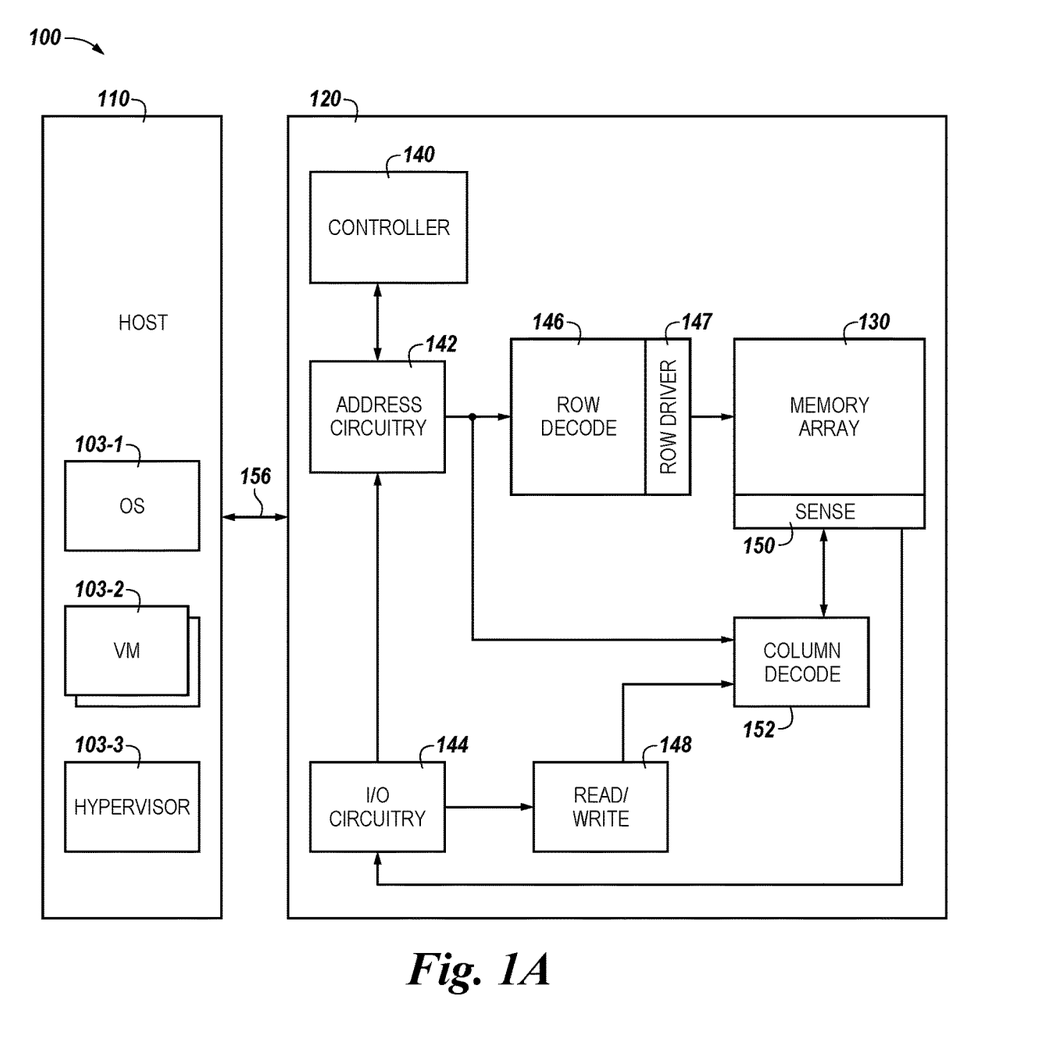
FIG. 1A is a block diagram of an apparatus in the form of a computing system including a memory device in accordance with a number of embodiments of the present disclosure.

FIG. 1A is a block diagram of an apparatus in the form of a computing system 100 including a memory device 120 in accordance with a number of embodiments of the present disclosure. As used herein, a memory device 120, a memory array 130, and/or host 110, for example, might also be separately considered an "apparatus."

In this example, system 100 includes a host 110 coupled to memory device 120 via an interface 156. The computing system 100 can be a personal laptop computer, a desktop computer, a digital camera, a mobile telephone, a memory card reader, or an Internet-of-Things (IoT) enabled device, among various other types of systems. Host 110 can include a number of processing resources (e.g., one or more processors, microprocessors, or some other type of controlling circuitry) capable of accessing memory 120. The system 100 can include separate integrated circuits, or both the host 110 and the memory device 120 can be on the same integrated circuit. For example, the host 110 may be a system controller of a memory system comprising multiple memory devices 120, with the system controller 110 providing access to the respective memory devices 120 by another processing resource such as a central processing unit (CPU).

In the example shown in FIG. 1, the host 110 is responsible for executing an operating system (OS) 103-1, a plurality of VMs 103-2, and a hypervisor 103-3. Although in various examples, the host 110 can be responsible for executing the OS and/or various applications that can be loaded thereto (e.g., from memory device 120 via controller 140). In other embodiments, the hypervisor 103-3 can include hardware or firmware and may not be executed by the host 110. In some examples, the OS 103-1 can be executed by the one or more of the VMs 103-2 and the hypervisor 103-3 hosted by a host 110.

For clarity, the system 100 has been simplified to focus on features with particular relevance to the present disclosure. The memory array 130 can be a DRAM array, SRAM array, STT RAM array, PCRAM array, TRAM array, RRAM array, NAND flash array, and/or NOR flash array, for instance. The array 130 can comprise memory cells arranged in rows coupled by access lines (which may be referred to herein as word lines or select lines) and columns coupled by sense lines (which may be referred to herein as digit lines or data lines). Although a single array 130 is shown in FIG. 1, embodiments are not so limited. For instance, memory device 120 may include a number of arrays 130 (e.g., a number of banks of DRAM cells).

The memory device 120 includes address circuitry 142 to latch address signals provided over an interface 156. The interface can include, for example, a physical interface employing a suitable protocol (e.g., a data bus, an address bus, and a command bus, or a combined data/address/command bus). Such protocol may be custom or proprietary, or the interface 156 may employ a standardized protocol, such as Peripheral Component Interconnect Express (PCIe), Gen-Z, CCIX, or the like. Address signals are received and 103 decoded by a row decoder 146 and a column decoder 152 to access the memory array 130. Data can be read from memory array 130 by sensing voltage and/or current changes on the sense lines using sensing circuitry 150. The sensing circuitry 150 can comprise, for example, sense amplifiers that can read and latch a page (e.g., row) of data from the memory array 130. The I/O circuitry 144 can be used for bi-directional data communication with host 110 over the interface 156. The read/write circuitry 148 is used to write data to the memory array 130 or read data from the memory array 130. As an example, the circuitry 148 can comprise various drivers, latch circuitry, etc.

Controller 140 decodes signals provided by the host 110. These signals can include chip enable signals, write enable signals, and address latch signals that are used to control operations performed on the memory array 130, including data read, data write, and data erase operations. In various embodiments, the controller 140 is responsible for executing instructions from the host 110. The controller 140 can comprise a state machine, a sequencer, and/or some other type of control circuitry, which may be implemented in the form of hardware, firmware, or software, or any combination of the three.

In accordance with various embodiments, the controller 140 can be configured to decode a security mode initialization command received thereto. The security mode initialization command can be received from the host 110 (e.g., as instructed by the hypervisor 103-3). The security mode initialization command can be provided to the memory device 120 to set a security mode of the memory device 120 and/or to designate one or more protected regions of the memory device 120. A security mode can include a locked mode and an unlocked mode, among other possible security modes. The memory device 120 can be configured to provide access to a protected region of the memory array 130 if the memory device 120 is in an unlocked mode or to prevent access to the protected region of the memory array 130 if the memory device 120 is in a locked mode.

The hypervisor 103-3, as executed by the host 110, can initialize the security mode initialization command to store a plurality of keys and a plurality of addresses or a plurality of ranges of addresses of the memory array 130 in a plurality of registers of the controller 140. The stored keys and addresses can define the protected regions of the memory array 130. The hypervisor 103-3 can initialize the security mode initialization command during an initialization of the system 100 or a time after the system is initialized.

In various examples, the protected regions can be defined by providing a single security mode initialization command or by providing a plurality of security mode initialization commands. For example, a first security mode initialization command can define a first protected region and a second security mode initialization command can define a second protected region of a memory array. The security mode initialization commands can be provided by the hypervisor 103-3 and/or by a combination of the hypervisor 103-3 and the VMs 103-2. For example, a first security mode initialization command can be provided by the hypervisor 103-3, a second security mode initialization command can be provided by a first VM from the VMs 103-2, and a third security mode initialization command can be provided by a second VM from the VMs 103-2.

In examples where a hypervisor defines the plurality of protected regions by initializing a security mode initialization command, the hypervisor can assign a key to each of the protected regions. The hypervisor can then manage the keys by assigning the keys to the VMs 103-2. For example, a hypervisor can assign a first protected region to a first VM and provide the first key corresponding to the first protected region to the first VM. The hypervisor can assign a second protected region to a second VM and provide the second key corresponding to the second protected region to the second VM. The hypervisor can assign itself a third protected region and retain a third key corresponding to the third protected region.

In examples where the hypervisor defines a single protected region to be used by itself and the VMs 103-2 define their own protected regions, the hypervisor may be unaware of the addresses corresponding to the protected regions managed by the VMs 103-2. The Hypervisor may also be unaware of the keys corresponding to the protected regions.

The keys can be a security token used to gain access to protected regions of the memory array 130. The keys can be encrypted or unencrypted. The keys can be provided by the hypervisor 103-3 and/or by the VMs 103-2 hosted by the hypervisor 103 to access the protected regions of the memory array 130. The keys can be unique to a protected region of memory and/or can be associated with a plurality of protected regions of memory. As described further below, the key can comprise one or more bits which can be stored in one or more registers of the memory device 120.

The protected regions of the memory array 130 describe regions of the memory array 130 that are protected using the keys. Each protected range of addresses can be defined by a first memory address and a second memory address. The first memory address can be a starting address and the second memory address can be an ending address. In various examples, a protected range is stored as a starting address and as an offset. The offset together with the starting address can be used to generate the ending address. The protected region can be continuous from the starting address to the ending address. In various examples, a protected region can be discontinuous and may be described by multiple sets of starting addresses and ending addresses.

In various examples, the memory array 130 can comprise one or more protected regions. Each of the protected regions can be defined using a starting address and an offset. Each of the starting addresses corresponding to a different protected region can be unique and/or can be a same starting address. Each of the offsets of the protected regions can also be a same offset or a different offset.

In various instances, the host 110 can provide an access command to the memory device 120. The access command can be provided from the hypervisor 103-3 and/or the VMs 103-2 via the host 110. The access command can be provided to access a protected region from the plurality of protected regions of the memory device 120. The access command can be associated with an address or a range of addresses and a key. The memory device 120 can compare the provided address to each of the plurality of protected regions to determine whether the address is within any of the protected regions (e.g., any of the protected ranges). If the address is within a protected region, the memory device 120 can compare the key with a stored key corresponding to the protected region to determine whether the key and the stored key match. If the key matches the stored key, then the memory device 120 can enter an unlocked mode from a locked mode, where the unlocked mode corresponds to the protected region and not to the other protected regions from the plurality of protected regions.

For example, if the key corresponding to the access command matches the stored key corresponding to an identified protected region from the plurality of protected regions, then the identified protected region can be unlocked while other protected regions from the plurality of protected regions remain in a locked mode. For instance, if an access command to a first protected region is verified, then the first protected region can be unlocked while a second and third protected regions remain locked.

In various examples, the address corresponding to the access command can be within a first protected region and a second protected region. A third key corresponding to the access command can match a first key corresponding to the first protected region and may not match a second key corresponding to the second protected region. The first protected region can be unlocked and the second protected region can remain locked.

The memory device 120 can, via the controller 140, enable a row driver to activate a row of the memory array 130 corresponding to the address (e.g., protected region). If the key does not match, the memory device 120 can, via the controller 140, prevent access to the protected region by preventing enablement of the row driver 147 of the memory array 130, thus preventing activation of a row corresponding to the access command.

Figure 1B:
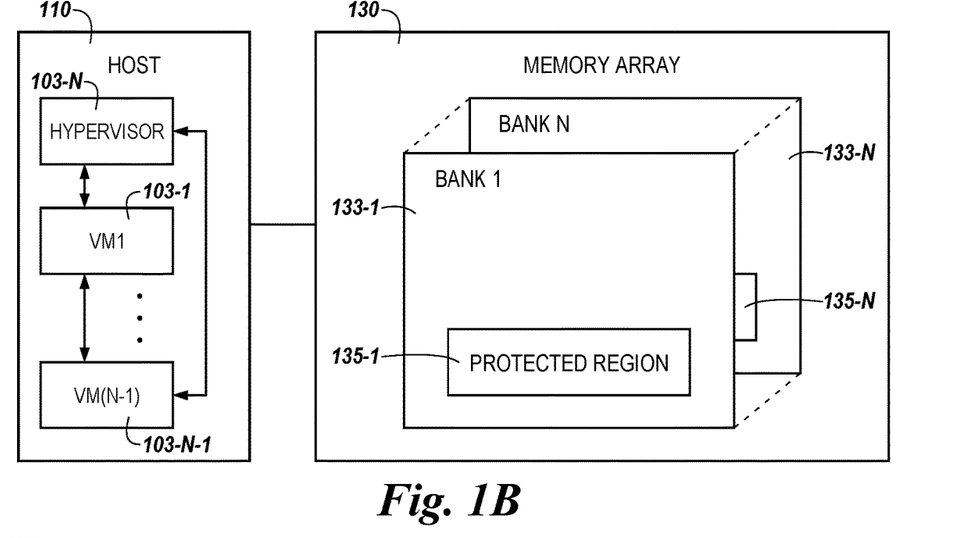
FIG. 1B is a block diagram of an apparatus in the form of a memory array including a plurality of banks in accordance with a number of embodiments of the present disclosure.

FIG. 1B is a block diagram of an apparatus in the form of a memory array 130 including a plurality of banks in accordance with a number of embodiments of the present disclosure. The memory array 130 can include a plurality of banks. For example, the memory array 130 includes the banks 133-1 to 133-N which can be referred to as banks 133. FIG. 1B also shows the host 110 coupled to the memory array 130. The host 110 can host the VMs 103-1 to 103-N-1 and the hypervisor 103-N.

Each of the banks 133 can include a protected region. For example, the bank 133-1 includes the protected region 135-1, . . . , and the bank 133-N includes the protected region 135-N. The protected regions 135-1 to 135-N can be referred to as protected regions 135. Accordingly, the memory array 130 can include the protected regions 135 where each of the protected regions 135 corresponds to a bank from the banks 133. Although not shown, in some examples, each of the banks 133 can include two or more protected regions.

In various embodiments, each of the protected regions 135 can correspond to the VMs 103-1 to 103-N-1 and/or the hypervisor 103-N. For example, the protected region 135-1 can correspond to the VM 103-1, . . . , the protected region 135-N-1 can correspond to the VM 103-N-1, and the protected region 135-N can correspond to the hypervisor 103-N. The VMs 103-1 to 103-N-1 can be coupled to each other and the hypervisor 103-N to allow for the assigning of the protected regions 135 and the providing of the keys corresponding to the protected regions 135.

Figure 2:
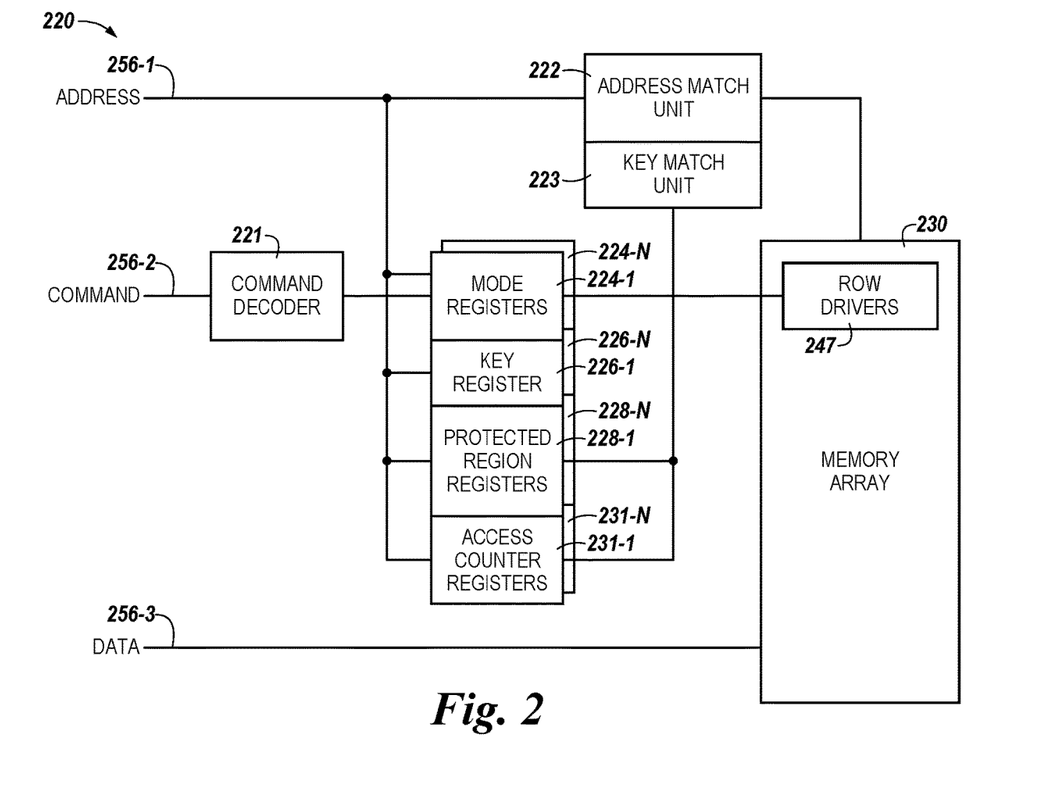
FIG. 2 is a block diagram of an apparatus in the form of a memory device including a memory array and portions of a controller capable of protecting regions of memory using a key in accordance with a number of embodiments of the present disclosure.

FIG. 2 is a block diagram of an apparatus in the form of a memory device 220 including a memory array 230 and portions of a controller capable of protecting regions of memory using a key in accordance with a number of embodiments of the present disclosure. The memory device 220 can be analogous to the memory device 120 in FIG. 1. The memory device 220 includes the memory array 230 and portions of a controller such as the controller 140 in FIG. 1.

The controller can include a command decoder 221, mode registers 224-1 to 224-N, key registers 226-1 to 226-N, protected region registers 228, and an access counter register 231. The controller can also include the address match unit 222 and a key match unit 223. Each of the mode registers 224-1 to 224-N, key registers 226-1 to 226-N, protected region registers 228-1 to 228-N, and access counter registers 231-1 to 231-N can be associate with a different protected region and/or bank of the memory array 230. For example, the mode registers 224-1, the key registers 226-1, the protected region registers 228-1, and the access counter registers 231-1 correspond to a first protected region, . . . , and the mode registers 224-N, the key registers 226-N, the protected region registers 228-N, and the access counter registers 231-N correspond to an Nth protected region. As used herein, the mode registers 224-1 to 224-N, the key registers 226-1 to 226-N, the protected region registers 228-1 to 118-N, and access counter registers 231-1 to 231-N can be referred to as the mode registers 224, the key registers 236, the protected region registers 228, and the access counter registers 231, respectively.

In this example, the interface (e.g., 156 shown in FIG. 1) comprises an address bus 256-1, a command bus 256-2, and a data bus 256-3. The device 220 can receive the security mode initialization command and/or access commands along with keys via the command bus 256-2. The device 220 can receive addresses via the address bus 256-1, and data can be provided to/from the device 220 via the data bus 256-3.

A host can provide, via the command bus 256-2, the security mode initialization command to initialize a security mode of the memory device 220. The memory device 220 can receive the security mode initialization command at the command decoder 221. The command decoder 220 can decode the security mode initialization command.

In various examples, the security mode initialization command can be associated with one or more keys and a number of addresses received via the command bus 256-2 and the address bus 256-1.

The controller can store a key in the key registers 226 and can store the one or more addresses in the protected region registers 228. Each of the mode registers 224, the key registers 226, the protected region registers 228, and/or the access counter registers 231 can be comprised of one or more registers.

The one or more addresses can be stored in the protected region registers 228 as a starting address and an offset. The starting address can be stored in a first register of the protected regions registers 228 and the offset can be stored in a second register of the protected region registers 228. The starting address and the ending address can define a protected region of the memory array 230. As such, the regions to protect (e.g., protected regions) can be stored in the protected region registers 228.

The key can be stored in the key registers 226. In various examples, a plurality of keys can be stored in the key registers 226. Each of the plurality of keys can be associated with a different one of the plurality of protected regions stored in the protected region registers 228. The plurality of keys can be used to allow access to the protected regions. For example, a first key can be used to allow access to a first protected region and a second key can be used to allow access to a second protected region.

Responsive to storing the key in the key registers 226 and the address in the protected region registers 228, the controller can change a security mode of a corresponding protected region from an unlocked mode to a locked mode in the mode registers 224. Responsive to storing a plurality of keys in the key registers 226 and a plurality of addresses in the protected region registers 228, the controller can change a security mode of a corresponding plurality of protected regions from an unlocked mode to a locked mode in the mode registers 224. The mode registers 224 can include a plurality of security mode registers. The security mode registers can store a first value representing an unlocked mode or a second value representing a locked mode, among other possible modes, for each of the protected regions. The locked mode can be used to prevent access to protected regions of the memory array 230. An unlocked mode can be used to allow access to protected regions of the memory array 230.

In various examples, responsive to receipt of the security mode initialization command, the controller can set the access counter registers 231. For example, the access counter registers 231 can be set to zero. Each of the access counter registers 231 can provide a count of unauthorized access commands directed to a corresponding protected region of the memory array 230 (e.g., as defined by protected region registers 228).

The controller can also process access commands. For example, an access command received via the command bus 256-2 can be decoded by the command decoder 221. The address match unit 222 can receive an address corresponding to the access command. The address match unit 222 can determine whether the received address is within a protected region (e.g., as stored in the protected region registers 228) from a plurality of protected regions.

If the received address is in a protected region, then the controller, via the key match unit 223, can determine whether the key associated with the access command matches a key corresponding to the protected region. If the key associated with the access command matches the key corresponding to the protected region, then the controller can modify a mode register corresponding to the protected region from a locked mode to an unlocked mode.

The controller can provide a signal to the row drivers 247 to activate a row corresponding to the received address if a mode register corresponding to the protected region reflects an unlocked mode. The controller can prevent a signal from being provided to the row drivers 247 if the mode registers 224 reflect a locked mode. Although the row drivers 247 are shown as being in the memory array 230, the row drivers 247 can also be implemented externally to the memory array 230 as shown in FIG. 1.

The controller can also include the access counter registers 231. The access counter register can store a count corresponding to a quantity of unauthorized access commands received at the memory device 220, where the access commands are associated with an address of at least one of the protected regions. The access counter registers 231 can be accessed to determine whether unauthorized access commands have been received by the memory device 220.

Figure 3:
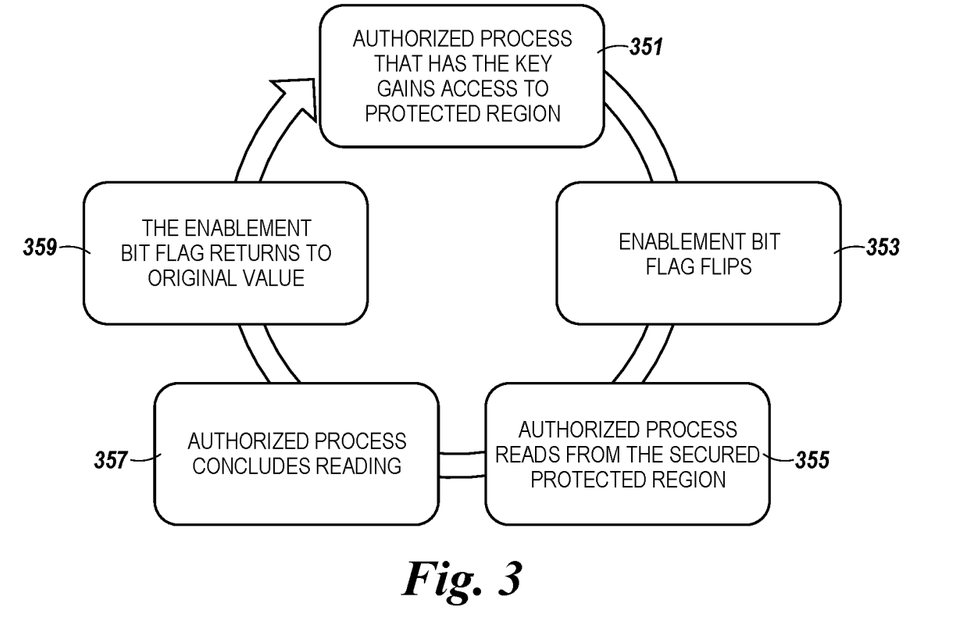
FIG. 3 illustrates an example flow diagram of a method for accessing protected regions of a memory array in accordance with a number of embodiments of the present disclosure.

FIG. 3 illustrates an example flow diagram of a method for accessing a protected region of a memory array in accordance with a number of embodiments of the present disclosure. At 351, the authorized process that has the key gains access to the protected region. The process can be an instance of a program that is being executed by the host such as an application process. For example, the process can be a VM, a hypervisor, and/or a different application, among other possible processes. The process can be authorized upon verifying that a key associated with an access command matches a stored key in one of the key registers and that an address corresponding to the process is within a corresponding protected region from a plurality of protected regions.

At 353, the enablement bit flag can be flipped. The enablement bit flag can be stored in a security mode register shown in FIG. 2 as one of the mode registers 224. The security mode register can correspond to the protected region such that changing the value of the security mode register modifies the security mode of the protected region and does not modify a security mode of different protected regions from the plurality of protected region. The enablement bit flag can be flipped from a locked mode to an unlocked mode. At 355, the authorized process can read from the protected region. An access command can be a read command or a write command, among other possible access commands. The controller can prevent enabling a row driver from activating a row responsive to the enablement bit flag indicating the locked mode, where the row corresponds to a received address associated with the access command. For example, the controller can prevent any row driver enablement when the mode bit indicated that a secured memory region is locked.

At 357, the authorized process can conclude reading from the protected region. At 359, the controller can return the enablement bit flag to its original value. For example, the enablement bit flag can be returned to a locked mode.

In various embodiments, a hypervisor can initiate a security mode initialization command. The security mode initialization command can be provided by the hypervisor to define one or more protected regions of a memory array and to associate keys with the one or more protected regions.

Defining protected regions utilizing the security mode initialization command provides the hypervisor flexibility. The hypervisor can have flexibility to define the size and content of the protected regions of the memory array and/or to allow VMs to define the size and content of the protected regions. For example, the hypervisor can define one or more of the protected regions as comprising a first size or a second size, among a number of possible sizes. The hypervisor and/or the VMs can activate a security mode by providing the security mode initialization command or can refrain from activating the security mode by refraining from providing security mode initialization commands to the memory device. For example, the hypervisor and a first VM can activate a security mode for a first protected region and a second protected region, respectively, while a second VM can refrain from activating the security mode corresponding to a third protected region.

A memory device can function in a security mode or without the security mode based on the hypervisor's selection. Further, the hypervisor or a VM can define a size or location of the protected region after the protected region has been initialized. For example, after initialization of a security mode, the hypervisor can increase the size of the protected region or decrease the size of the protected region. After initialization of a security mode, the hypervisor or a VM can also change a base address of the protected region and/or an offset of the protected region. The hypervisor or a VM can also exit the security mode after the memory device has been placed in the security mode. For example, the hypervisor can store a predefined value in the protected region registers. The hypervisor can store a zero as a base address and/or an offset of the protected region to exit the security mode. The memory device can set a corresponding mode register to an unlocked mode responsive to identifying that a base address and/or an offset of the protected region has a zero value.

The hypervisor can utilize an application programming interface (API) to generate the security mode initialization command and/or an access command used to define and/or access a protected region of the memory array. The hypervisor can comply with the security features of the memory device utilizing the API.

In various examples, the security mode initialization command can be generated by the hypervisor and/or a VM and can be received by the memory device as part of an initialization process of a computing device, a VM, and/or the hypervisor. The memory device can store a key in a key register from a plurality of key registers responsive to receiving the security mode initialization command. The memory device can store an address of a memory device in one of the protected region registers. In various examples, each of the key registers can be associated with a different one of the protected region registers and/or mode registers. Such that the key is stored in a key register that is associated with a protected region register that stored the address. The key register and the protected region register can correspond to a protected region of a bank. As such, each of the key registers and the protected region registers can be uniquely associated with a different bank of a memory array or a memory device.

The memory device can set a mode register based on the storing of the key and/or the storing of the address. The mode register can identify whether a protected region of the memory array is protected. The memory device can set the mode register to a locked mode. The locked mode can be a protected mode.

Figure 4:
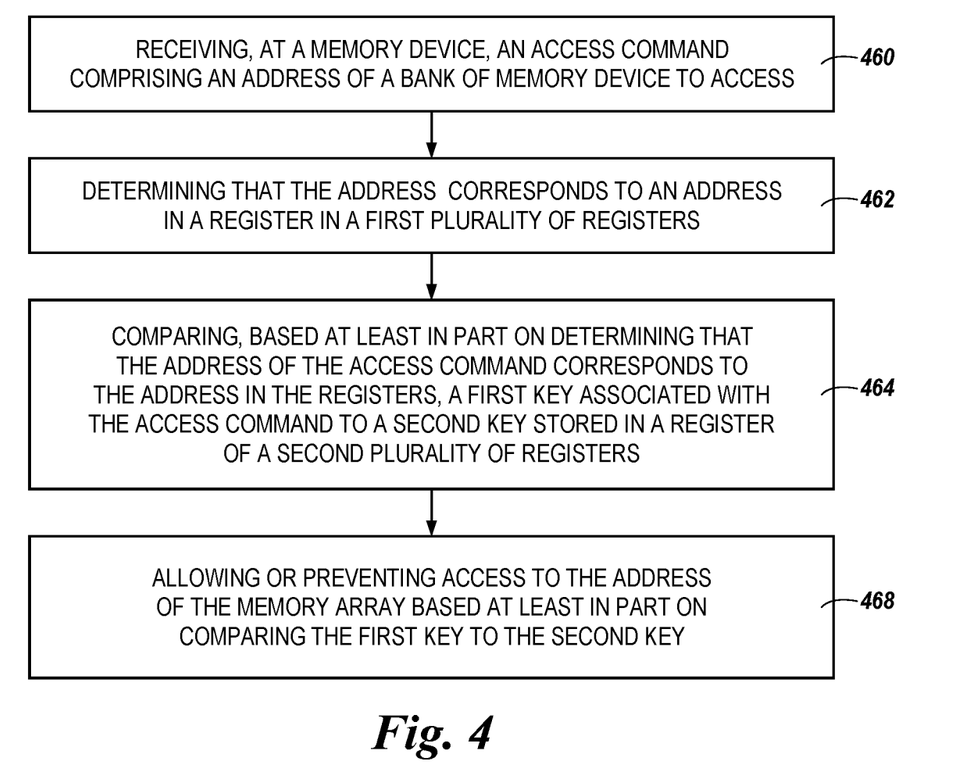
FIG. 4 illustrates an example flow diagram of a method for accessing protected regions of a memory array in accordance with a number of embodiments of the present disclosure.

FIG. 4 illustrates an example flow diagram of a method for accessing a protected region of a memory array in accordance with a number of embodiments of the present disclosure. The method can be executed by a memory device of a computing system.

At 460, a memory device can receive an access command comprising an address of a bank of a memory device to access. At 462, a determination can be made as to whether the address corresponds to an address in a register in a first plurality of registers. The address in a register can define a protected region corresponding to the bank from a plurality of protected regions of the memory device as indicated by a plurality of protected region registers. The address can be within the protected region if the address is greater than a starting address of the protected region but less than the ending address of the protected region. In various examples, the access command can be associated with a plurality of addresses to access. The plurality of addresses can be within the protected region if at least one of the plurality of addresses is greater than a starting address and at least one of the of the plurality of addresses is less than the ending address of the protected region.

At 464, the memory device can compare, based at least in part on determining that the address of the access command corresponds to the address in the registers, a first key associated with the access command to a second key stored in a register of a second plurality of registers. For example, responsive to determining that the address is within the protected region, the controller can determine whether a received key associated with the access command, from a plurality of keys associated with the plurality of protected regions, matches a key stored in plurality of key registers. The received key can match the stored key if the received key is equal to the stored key or if the received key is substantially equal to the stored key. The received key can match the stored key if the stored key can be derived from the received key, among other examples.

At 468, the memory device can allow or prevent access to the address of the memory array based at least in part on comparing the first key to the second key. For example, responsive to determining that the received key matches the stored key, the controller can allow access to the address of the memory array. The memory device can allow access to the address by providing, to the host, the data stored at memory cells corresponding to the address. Access can be allowed by permitting an activation of a row of the array corresponding to the address. The method can further allow activation of a row to which the address corresponds by switching an access enable flag from a first state to a second state, wherein rows corresponding to addresses within the protected region are not activatable unless the access enable flag is in the second state. Subsequent to execution of the access command (e.g., read command), the access enable flag can be returned to the first state to prevent activation of rows corresponding to the protected region. Responsive to determining that the received key does not match the stored key, the controller can prevent access to the address of the memory array. Responsive to determining that the address is outside the protected region, the controller can allow access to the address without performing a key match comparison.

In various examples, the stored key can correspond to the specific region (e.g., protected region) of the bank. The stored key and the protected region can be assigned to a VM by a hypervisor. The stored key and the protected region can be assigned to the hypervisor. The stored key and the protected regions can be assigned to one or more of the VMs and the hypervisor. In various embodiments, one or more of the key registers, protected region registers, and/or mode registers can be written to by a first device and can be accessed by a second device. For example, the key registers can be written to by a processing resource external to the memory device and may be read by the memory device itself. The processing resource external to the memory device may execute instructions corresponding to a hypervisor and/or a VM to store one or more keys in the key registers. However, the processing resource may not be provided access to the data stored in the key registers. The key registers may only be access from a device internal to (e.g., within) the memory device. For example, the key registers may only be accessed from a controller internal to the memory device.

In various examples, the protected region can store a kernel of the hypervisor and/or a kernel of the VM. Each of the protected regions corresponding to a different bank can store a different kernel corresponding to the hypervisor and the VMs.

In various instances, a hypervisor can provide the keys and addresses corresponding to the protected regions via a security mode initialization command to define the protected regions and place the protected regions in a locked mode. The hypervisor can define the protected regions at startup, for example. The hypervisor can then initiate a plurality of VMs. The hypervisor can then assign the protected regions to the VMs such that each protected region corresponds to a different VM. The assignment of protected regions to VMs can occur at run time. The hypervisor can continue to manage the protected regions after assigning the protected regions to the VMs. For example, responsive to initiating a new VM and deleting a previously initiated VM, the hypervisor can reassign a protected region to the newly initiated VM from the previously initiated VM. The hypervisor can provide the password and the addresses defining the previously initiated VM to the newly initiated VM. In various examples, the hypervisor can generate a new key and associate the new key with the protected region prior to assigning the new key and the protected region to the newly initiated VM. The hypervisor can also redefine the protected region by providing a new starting address and/or a new ending address. The hypervisor can provide the redefined protected region to the newly initiated VM. Redefining the protected region can prevent other VMs previously assigned the protected region from accessing the redefined protected region.

In various instances, a host can be configured to host a plurality of virtual machines (VMs). A memory resource can be coupled to the host and shared by the plurality of VMs. The memory resource can comprise a plurality of regions each allocated to respective ones of the plurality of VMs and each having a respective key associated therewith, and wherein a respective address space of each region is unique relative to the other regions of the plurality of regions The memory resource can be configured to receive an access command from one of the plurality of VMs, compare a key associated with the received access command to the key associated with one region of the plurality of regions, and allow or prevent access to the one region of the plurality based at least in part on comparing the key associated with the received access command to the key associated with the one region of the plurality of regions.

The host can further be configured to host a hypervisor and wherein the hypervisor is configured to assign a plurality of keys corresponding to the plurality of regions to the plurality of VMs. The hypervisor can be configured to assign the plurality of regions and the plurality of keys to the plurality of VMs at startup. The hypervisor can also assign the plurality of regions and the plurality of keys to the plurality of VMs responsive to a creation of the plurality of VMs.

In various examples, the hypervisor can be configured to assign the plurality of regions and the plurality of keys to the plurality of VMs utilizing a command that initializes a security mode provided to the memory resource. The VMs can also be configured to generate and store a plurality of keys corresponding to the plurality of regions in the memory resource.

In various instances, an apparatus (e.g., memory device) can comprise a first plurality of registers configured to store a plurality of keys used to determine whether access commands are allowed access to a plurality of regions of the apparatus, a second plurality of registers configured to store a plurality of addresses defining the plurality of regions, and a control circuitry. The control circuitry can be configured to, responsive to receiving a command to initiate a mode of operation, store the plurality of keys in the first plurality of registers and store the plurality of addresses of the apparatus in the second plurality of registers, wherein the plurality of addresses and the plurality of keys correspond to the plurality of regions. The control circuitry can also be configured to, responsive to receiving the command to initiate the mode of operation, control access to a different address corresponding to an access command based on whether the different address is within a region from the plurality of protected regions and based on whether a different key corresponding to the access command matches a corresponding one of the plurality of keys stored in the first plurality.

In some examples, each of the plurality of regions can correspond to a different bank of the apparatus. The control circuitry can be configured to receive the command to initiate the mode of operation from a hypervisor. The control circuitry can also be configured to receive the access command in response to signaling from a VM. The region can further be configured to store a kernel of the VM.

The control circuitry can further be configured to receive the access command in response to signaling from a hypervisor. The region can be configured to store a kernel of the hypervisor. In an example, the plurality of keys and a portion of the plurality of addresses are associated with a hypervisor assignment for a plurality of VMs. The hypervisor can assign the plurality of keys and a portion of the plurality of addresses to the plurality of VM such the hypervisor portions and assigns the protected regions. The hypervisor can reserve a key from the plurality of keys and an address from the plurality of addresses for its use. In some instances each of the plurality of keys can be associated with a different one of the plurality of addresses and corresponds to a different one of the plurality of regions.

Figure 5:
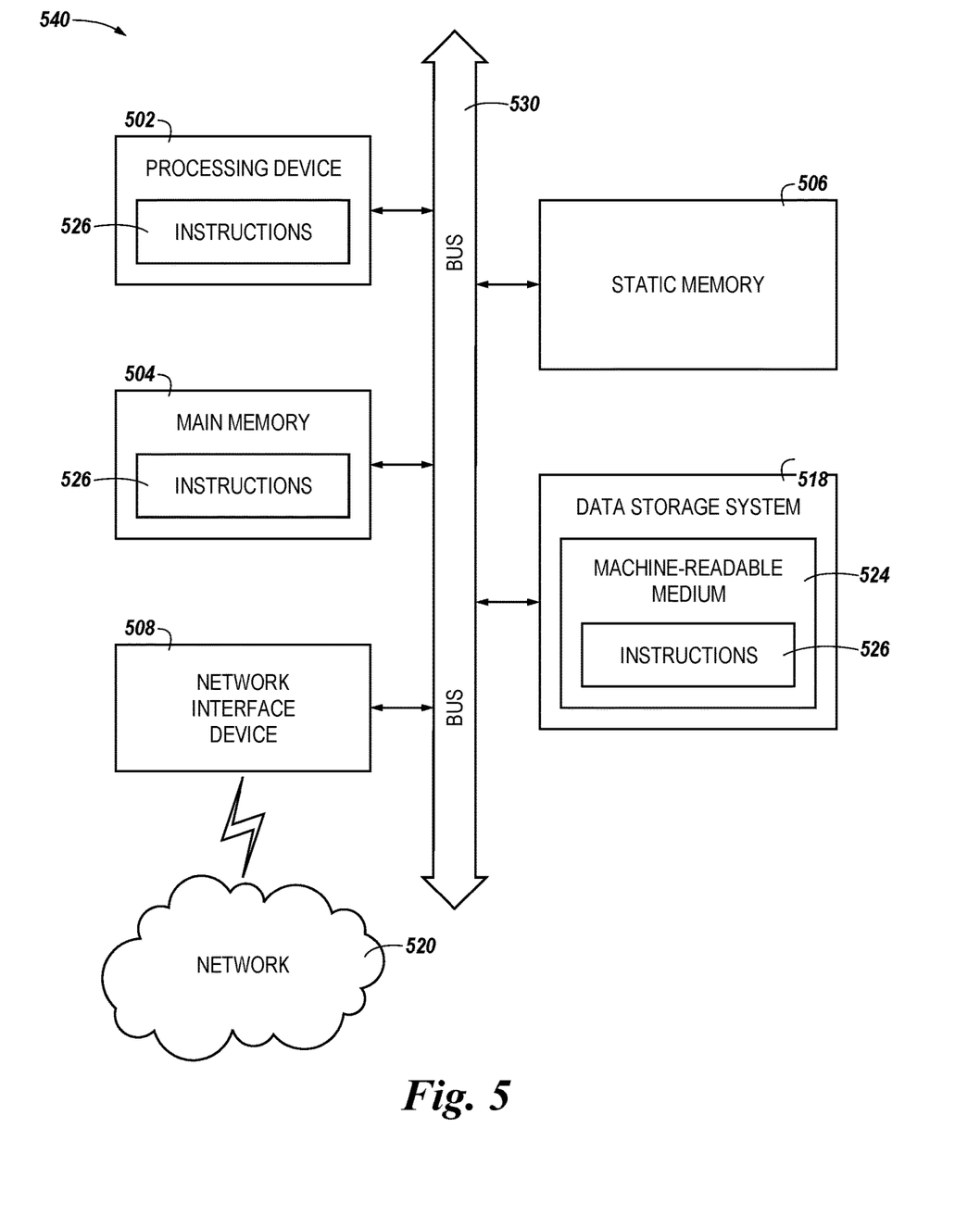
FIG. 5 illustrates an example machine of a computer system within which a set of instructions, for causing the machine to perform various methodologies discussed herein, can be executed.

FIG. 5 illustrates an example machine of a computer system 540 within which a set of instructions, causing the machine to perform one or more of the methodologies discussed herein, can be executed. In various embodiments, the computer system 540 can correspond to a host system (e.g., the system 110 of FIG. 1) that includes, is coupled to, or utilizes a memory sub-system (e.g., the memory device 120 of FIG. 1) or can be used to perform the operations of a controller (e.g., the controller 140 of FIG. 1, including the register 224, 226,228, and 231 of FIG. 2). In alternative embodiments, the machine can be connected (e.g., networked) to other machines in a LAN, an intranet, an extranet, and/or the Internet. The machine can operate in the capacity of a server or a client machine in client-server network environment, as a peer machine in a peer-to-peer (or distributed) network environment, or as a server or a client machine in a cloud computing infrastructure or environment.

The machine can be a personal computer (PC), a tablet PC, a set-top box (STB), a Personal Digital Assistant (PDA), a cellular telephone, a web appliance, a server, a network router, a switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform one or more of the methodologies discussed herein.

The example computer system 540 includes a processing device 502, a main memory 504 (e.g., read-only memory (ROM), flash memory, dynamic random-access memory (DRAM) such as synchronous DRAM (SDRAM) or Rambus DRAM (RDRAM), etc.), a static memory 506 (e.g., flash memory, static random-access memory (SRAM), etc.), and a data storage system 518, which communicate with each other via a bus 530.

Processing device 502 represents one or more general-purpose processing devices such as a microprocessor, a central processing unit, or the like. More particularly, the processing device can be a complex instruction set computing (CISC) microprocessor, reduced instruction set computing (RISC) microprocessor, very long instruction word (VLIW) microprocessor, or a processor implementing other instruction sets, or processors implementing a combination of instruction sets. Processing device 502 can also be one or more special-purpose processing devices such as an application specific integrated circuit (ASIC), a field programmable gate array (FPGA), a digital signal processor (DSP), network processor, or the like. The processing device 502 is configured to execute instructions 526 for performing the operations and steps discussed herein. The computer system 540 can further include a network interface device 508 to communicate over the network 520.

The data storage system 518 can include a machine-readable storage medium 524 (also known as a computer-readable medium) on which is stored one or more sets of instructions 526 or software embodying one or more of the methodologies or functions described herein. The instructions 526 can also reside, completely or at least partially, within the main memory 504 and/or within the processing device 502 during execution thereof by the computer system 540, the main memory 504 and the processing device 502 also constituting machine-readable storage media.

In one embodiment, the instructions 526 include instructions to implement functionality corresponding to the controller 140 of FIG. 1. While the machine-readable storage medium 524 is shown in an example embodiment to be a single medium, the term "machine-readable storage medium" should be taken to include a single medium or multiple media that store the one or more sets of instructions. The term "machine-readable storage medium" shall also be taken to include any medium that is capable of storing or encoding a set of instructions for execution by the machine and that cause the machine to perform one or more of the methodologies of the present disclosure. The term "machine-readable storage medium" shall accordingly be taken to include, but not be limited to, solid-state memories, optical media, and magnetic media.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure. It is to be understood that the above description has been made in an illustrative fashion, and not a restrictive one. Combinations of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:
   a first plurality of registers configured to store a plurality of keys used to determine whether access commands are allowed access to a plurality of regions of the apparatus;
   a second plurality of registers configured to store a plurality of addresses defining the plurality of regions; and
   control circuitry configured to:
      responsive to receiving a command to initiate a mode of operation:
         store the plurality of keys in the first plurality of registers;
         store the plurality of addresses of the apparatus in the second plurality of registers, wherein the plurality of addresses and the plurality of keys correspond to the plurality of regions; and
      control access to a different address corresponding to an access command, based on whether the different address is within a region from the plurality of regions and based on whether a different key corresponding to the access command matches a corresponding one key of the plurality of keys stored in the first plurality of registers, by:
         determining whether the different address is within the region;
         comparing the different key to the corresponding one key of the plurality of keys; and
         responsive to determining that the different address is in the region and that the different key matches the corresponding one key of the plurality of keys, modifying a mode register corresponding to a corresponding one region of the plurality of regions from a locked mode to an unlocked mode.

2. The apparatus of claim 1, wherein each of the plurality of regions corresponds to a different bank of the apparatus.

3. The apparatus of claim 1, wherein the control circuitry is configured to receive the command to initiate the mode of operation from a hypervisor.

4. The apparatus of claim 1, wherein the control circuitry is configured to receive the access command in response to signaling from a virtual machine (VM).

5. The apparatus of claim 4, wherein the region is configured to store a kernel of the VM.

6. The apparatus of claim 1, wherein the control circuitry is configured to receive the access command in response to signaling from a hypervisor.

7. The apparatus of claim 6, wherein the region is configured to store a kernel of the hypervisor.

8. The apparatus of claim 1, wherein the plurality of keys and a portion of the plurality of addresses are associated with a hypervisor assignment for a plurality of VMs.

9. The apparatus of claim 8, wherein the hypervisor is configured to reserve a key from the plurality of keys and an address from the plurality of addresses for use by the hypervisor.

10. The apparatus of claim 1, wherein each of the plurality of keys is associated with a different one address of the plurality of addresses and corresponds to a different one region of the plurality of regions.

11. A method comprising:
    storing, in a first plurality of registers, a plurality of keys used to determine whether access commands are allowed access to a plurality of regions of a memory device;
    storing, in a second plurality of registers, a plurality of addresses defining the plurality of regions; and
    controlling access to a different address corresponding to an access command, based on whether the different address is within a region from the plurality of regions and based on whether a different key corresponding to the access command matches a corresponding one key of the plurality of keys stored in the first plurality of registers, by:
       determining whether the different address is within the region;
       comparing the different key to the corresponding one key of the plurality of keys; and
       responsive to determining that the different address is in the region and that the different key matches the corresponding one key of the plurality of keys, modifying a mode register corresponding to a corresponding one region of the plurality of regions from a locked mode to an unlocked mode.

12. The method of claim 11, further comprising:
    storing, in the first plurality of registers, the plurality of keys wherein each of the plurality of keys correspond to a different virtual machine (VM) from a plurality of VMs; and
    storing, in the second plurality of registers, the plurality of addresses defining the plurality of regions wherein each of the plurality of regions corresponds to a different one VM of the plurality of VMs.

13. The method of claim 11, further comprising providing access to the corresponding one region of the plurality of regions responsive to the mode register being in an unlocked mode.

14. The method of claim 11, further comprising:
    responsive to determining that the different address is in the region and that the different key matches the corresponding one key of the plurality of keys, modifying a mode register corresponding to a corresponding one region of the plurality of regions from a locked mode to an unlocked mode; and responsive to determining that the different address is in the region and that the different key matches the corresponding one key of the plurality of keys, refraining from modifying a plurality of mode registers corresponding to other regions from the plurality of regions such that the plurality of mode registers remain in a locked mode.

15. An apparatus, comprising:

a first plurality of registers configured to store a plurality of keys used to determine whether access commands are allowed access to a plurality of regions of the apparatus;

a second plurality of registers configured to store a plurality of addresses defining the plurality of regions; and control circuitry configured to:
responsive to receiving a command to initiate a mode of operation:
store the plurality of keys in the first plurality of registers;
store the plurality of addresses of the apparatus in the second plurality of registers; and provide access to a different address corresponding to an access command if the different address is within a region from the plurality of regions and if a different key corresponding to the access command matches a corresponding one key of the plurality of keys stored in the first plurality of registers by providing a signal to a row driver to activate a row corresponding to the different address; and prevent the signal from being provided to the row driver if the different address is within the region and if the different key does not match the corresponding one key of the plurality of keys.

16. The apparatus of claim 15, wherein the control circuitry is further configured to prevent access to the different address corresponding to the access command if the different address is within the region and if the different key corresponding to the access command does not match the corresponding one key of the plurality of keys stored in the first plurality of registers.

17. The apparatus of claim 15, wherein the control circuitry is further configured to provide access to the different address corresponding to the access command if the different address is not within the region from the plurality of regions.

* * * * *